United States Patent [19]
Dickson

[11] Patent Number: 5,740,797
[45] Date of Patent: Apr. 21, 1998

[54] CARDIAC SYNCHRONIZED VENTILATION

[75] Inventor: Eric W. Dickson, Worcester, Mass.

[73] Assignee: University of Massachusetts, Boston, Mass.

[21] Appl. No.: 606,412

[22] Filed: Feb. 23, 1996

[51] Int. Cl.$^6$ .................................................. A61M 16/00
[52] U.S. Cl. ........................ 128/204.28; 128/203.14; 128/204.18; 128/204.21; 128/204.23; 128/205.13; 128/205.14; 128/205.24
[58] Field of Search ........................ 128/203.12, 203.14, 128/204.18, 204.21, 204.23, 204.28, 204.25, 204.26, 205.11, 205.13, 205.14, 205.24, 661.09, 713, 716, 720, 721, 719, 725

[56] References Cited

U.S. PATENT DOCUMENTS

| | | | |
|---|---|---|---|
| 4,240,409 | 12/1980 | Robinson et al. | 600/16 |
| 4,351,344 | 9/1982 | Stenzler | 128/720 |
| 4,527,549 | 7/1985 | Gabbay | 600/18 |
| 4,787,368 | 11/1988 | Kageyama | 600/18 |
| 4,877,035 | 10/1989 | Bogen et al. | 128/713 |
| 5,020,516 | 6/1991 | Biondi et al. | 128/30.2 |
| 5,158,536 | 10/1992 | Sekins et al. | 604/20 |
| 5,159,935 | 11/1992 | Sackned et al. | 128/721 |
| 5,188,098 | 2/1993 | Hoffman et al. | |
| 5,335,650 | 8/1994 | Shaffer et al. | 128/200.24 |
| 5,350,359 | 9/1994 | Shaffer et al. | 604/51 |
| 5,353,788 | 10/1994 | Miles | 128/204.23 |
| 5,377,671 | 1/1995 | Biondi et al. | 128/204.23 |
| 5,429,123 | 7/1995 | Shaffer et al. | 128/204.23 |
| 5,437,272 | 8/1995 | Fuhrman | 128/201.12 |
| 5,443,504 | 8/1995 | Hill | 623/3 |
| 5,492,109 | 2/1996 | Hirschl et al. | 128/201.21 |
| 5,513,648 | 5/1996 | Jackson | 128/716 |
| 5,522,397 | 6/1996 | Vermaak | 128/716 |

OTHER PUBLICATIONS

Biondi, "Mechanical Heart–Lung Interaction in the Adult Respiratory Distress Syndrome", Adult Respiratory Distress Syndrome, 11:691–714, 1990.

Craver et al., "The Percutaneous Intraaortic Balloon Pump", 2189–2193.

Fuhrman, "Clinical Trials of Perfluorocarbon–Associated Gas Exchange", The Society fo Critical Care Medicine, 15:206–211, 1995.

Fuhrman, "Perfluorocarbon–associated gas exchange", Critical Care Medicine, 19: 712–722, 1991.

Hirschl et al., "Development and application of a simplified liquid ventilator", Critical Care Medicine, 23:157–163, 1995.

Pinsky et al., "Hemodynamic efects of cardiac cycle–specific increases in intrathoracic pressure", Cardiac Cycle–Specific Increases in ITP, pp. 604–612.

(List continued on next page.)

Primary Examiner—Vincent Millin
Assistant Examiner—William J. Deane, Jr.
Attorney, Agent, or Firm—Fish & Richardson P.C.

[57] ABSTRACT

A cardiac synchronized ventilator includes a balloon, a balloon pump arranged to inflate and deflate the balloon in synchrony with cardiac function, and a conversion unit. The conversion unit includes a chamber which is fillable with a ventilation medium and which contains the balloon and one or more conduction lines arranged to carry ventilation medium from the chamber to the patient's lungs and from the patient's lungs. Inflation of the balloon is synchronized to occur during systole and pressurizes the conduction line to deliver ventilation medium to the patient's lungs. Deflation of the balloon is synchronized to occur during diastole and negatively pressurizes the conduction line to remove ventilation medium from the patient's lungs. The pump is an intraaortic balloon pump. A conduit attached to a source of ventilation medium is in fluid communication with the conduction line. The ventilation medium may be a liquid or gas.

21 Claims, 5 Drawing Sheets

OTHER PUBLICATIONS

Scott, "Ventilators of Tomorrow Will Break New Ground" Advance for Respiratory Care Pracitioners, pp. 10–11 Dec. 14, 1992.

Shaffer et al., "Liquid Ventilation", Pediatric Pulmonology, 14:102–109, 1992.

Schulman et al., "Hemodynamic Effects of 1:2 ECG–Coupled Jet Ventilation in the Dog", pp. 819–825.

Zelano et al., "Comparison of an Extraaortic Counterpulsation Device Versus Intraortic Balloon Pumping In Severe Cardiac Failure", EACD Versus IABP, M342–M344.

5,740,797

CARDIAC SYNCHRONIZED VENTILATION

BACKGROUND OF THE INVENTION

This invention relates generally to ventilators, and, more particularly, to cardiac synchronized ventilators.

Positive intrathoracic pressure decreases venous return to the heart and unless compensated for by an increase in central venous pressure or unless it occurs during cardiac systole when venous return is minimal, it causes a net decrease in cardiac output. Negative intrathoracic pressure increases venous return, and thus increases cardiac output.

During normal spontaneous inspiration, negative intrathoracic pressure draws blood from the normobaric head, arms, and abdomen to the right side of the heart. This action fills the right heart and provides a normal cardiac output. On the other hand, during normal spontaneous expiration, positive intrathoracic pressure decreases right heart filling and momentarily decreases right heart cardiac output.

Standard mechanical ventilators are applied to patients with acute cardio-respiratory failure to assist pulmonary function. During mechanical ventilation, the positive pressure applied to force air into the lungs converts the normally negative intrathoracic pressure of inspiration to a positive pressure phase. The effect of this reversal can be devastating to the ailing heart since inspiration no longer assists venous return but instead impedes it. This can result in an unwanted and potentially dangerous interference with cardiac function. During mechanical ventilation, exhalation remains spontaneous and positive, thus intrathoracic pressure remains above barometric pressure throughout the respiratory cycle. Usual treatment for this unwanted effect includes increasing central venous pressure via intravenous fluids, thus forcing adequate volume to the right heart by an increased driving pressure. However, the administration of intravenous fluids can result in complications including ascites, pulmonary edema, electrolyte imbalances, and peripheral tissue edema.

A recent development in ventilation technology is the synchronization of the ventilator to the cardiac cycle. Monophasic cardiac synchronized ventilation delivers a positive pressure breath only during cardiac systole, a time when venous return is at zero, to prevent impedance of venous return. It has been shown that momentary positive pressure swings during systole assist emptying of the left heart. Compared to standard positive pressure ventilation, cardiac synchronized ventilation is usually carried out at a much higher rate and at lower tidal volumes. It has also been shown that a synchronized increase in thoracic pressure augments cardiac output.

Biondi et al., U.S. Pat. No. 5,377,671, describes biphasic cardiac synchronized ventilation which attempts to synchronize both systole and diastole with ventilation. A positive pressure breath producing positive intrathoracic pressure is delivered at systole to aid ventricle ejection, and a negative pressure breath producing negative intrathoracic pressure is instituted during diastole to assist with venous return. Although similar to a normal respiratory system, the phases are reversed in biphasic cardiac synchronized ventilation since inspiration is now positive and expiration negative. Mechanical negative pressure expiration with gas as the ventilation medium may have negative effects due to the closing of small airways trapping air during the negative pressure pulse.

SUMMARY OF THE INVENTION

This invention is based on the discovery that an intraaortic balloon pump can be modified for use as a cardiac synchronized ventilator.

In general, the invention features a cardiac synchronized ventilator for use with a patient. The ventilator includes a balloon, a balloon pump, for example, an intraaortic balloon pump, arranged to inflate and deflate the balloon, inflation of the balloon being in synchrony with cardiac function of the patient, and a conversion unit. The conversion unit includes a chamber which in use is filled with a ventilation medium and which contains the balloon, and one or more conduction lines for containing ventilation medium. The conduction lines are arranged to carry ventilation medium from the chamber to the patient's lungs and from the patient's lungs. The balloon is inflated during systole and the inflation pressurizes the conduction line to deliver ventilation medium to the patient's lungs.

The conduction lines include an inspiratory line connecting the chamber to the patient's lungs for conducting oxygenated ventilation medium to the patient's lungs, and an expiratory line for conducting deoxygenated ventilation medium from the patient's lungs. A conduit connected to a source of ventilation medium is in fluid communication with the conduction line. The inspiratory line, the expiratory line, and the conduit include valves preventing backflow of the ventilation medium. An additional valve, for example, a balloon valve, is synchronized to the balloon to close the expiratory line when the balloon is inflated.

In particular embodiments, the ventilation medium is a gas and the expiratory line conducts the gas from the patient's lungs to atmosphere upon deflation of the balloon. The ventilation source itself can be a ventilator able to control the synchronized valve to close the expiratory line, and the ventilator and the cardiac synchronized ventilator are constructed and arranged to ventilate the patient concurrently.

In particular embodiments, the ventilation medium is a liquid, e.g., oxygenated perfluorocarbon, and the source is a reservoir of the liquid. The expiratory line conducts the liquid from the patient's lungs to the reservoir upon deflation of the balloon.

The expiratory line conducts liquid ventilation medium from the patient's lungs to the chamber producing a closed system. In the closed system, deflation of the balloon during diastole negatively pressurizes the conduction line to remove ventilation medium from the patient's lungs. The deflation of the balloon is synchronized to occur during diastole.

The conduit can include a valve allowing uptake of liquid from the liquid reservoir to the conduction line at a first conduction line pressure, and delivery of liquid from the conduction line to the reservoir at a second conduction line pressure greater than the first conduction line pressure. A membrane oxygenator can be used to oxygenate the liquid.

According to another aspect of the invention, a balloon pump converter for converting an intraaortic balloon pump into a cardiac synchronized ventilator includes a conversion chamber for interfacing with the intraaortic balloon pump and for containing a balloon associated with the intraaortic balloon pump. The conversion chamber is fillable with ventilation medium, and a conduction line is connected to the chamber for conducting ventilation medium to and from a patient's lungs. The ventilation medium can be a liquid or gas.

According to another aspect of the invention, a ventilator capable of delivering liquid or gas to the pulmonary system of a patient includes a balloon, for example, an intraaortic balloon, a balloon pump for inflating and deflating the balloon, and a conversion unit including a chamber fillable with the gas or liquid and containing the balloon. A conduction line for containing the gas or liquid is arranged to carry the gas or liquid from the chamber to and from a patient's lungs. Inflation of the intraaortic balloon pressurizes the conduction line to deliver the gas or liquid to the patient's lungs.

Monophasic cardiac synchronized ventilation is the delivering of positive intrathoracic pressure only during ventricular systole and allowing for passive exhalation during diastole. This decreases the negative effect of mechanical ventilation on right heart venous return and assists the left ventricle with ejection. Liquid biphasic cardiac synchronized ventilation makes exhalation a negative pressure event, potentially augmenting cardiac output.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the preferred methods and materials are described below. All publications and patents mentioned herein are incorporated by reference in their entirety. In case of conflict, the present application, including definitions, will control. In addition, the materials, methods, and examples are illustrative only and not intended to be limiting.

Other features and advantages of the invention will be apparent from the following detained description, and from the claims.

DETAILED DESCRIPTION

The drawings are first briefly described.

Drawings

Intraaortic balloon pumps (IABP), such as a standard IABP available from, for example, Datascope, Montvale, N.J., are synchronized to the cardiac cycle. Utilizing this established technology, a novel conversion device is employed which modifies the IABP for use as a cardiac synchronized ventilator.

Gas Ventilation

Figure 1:
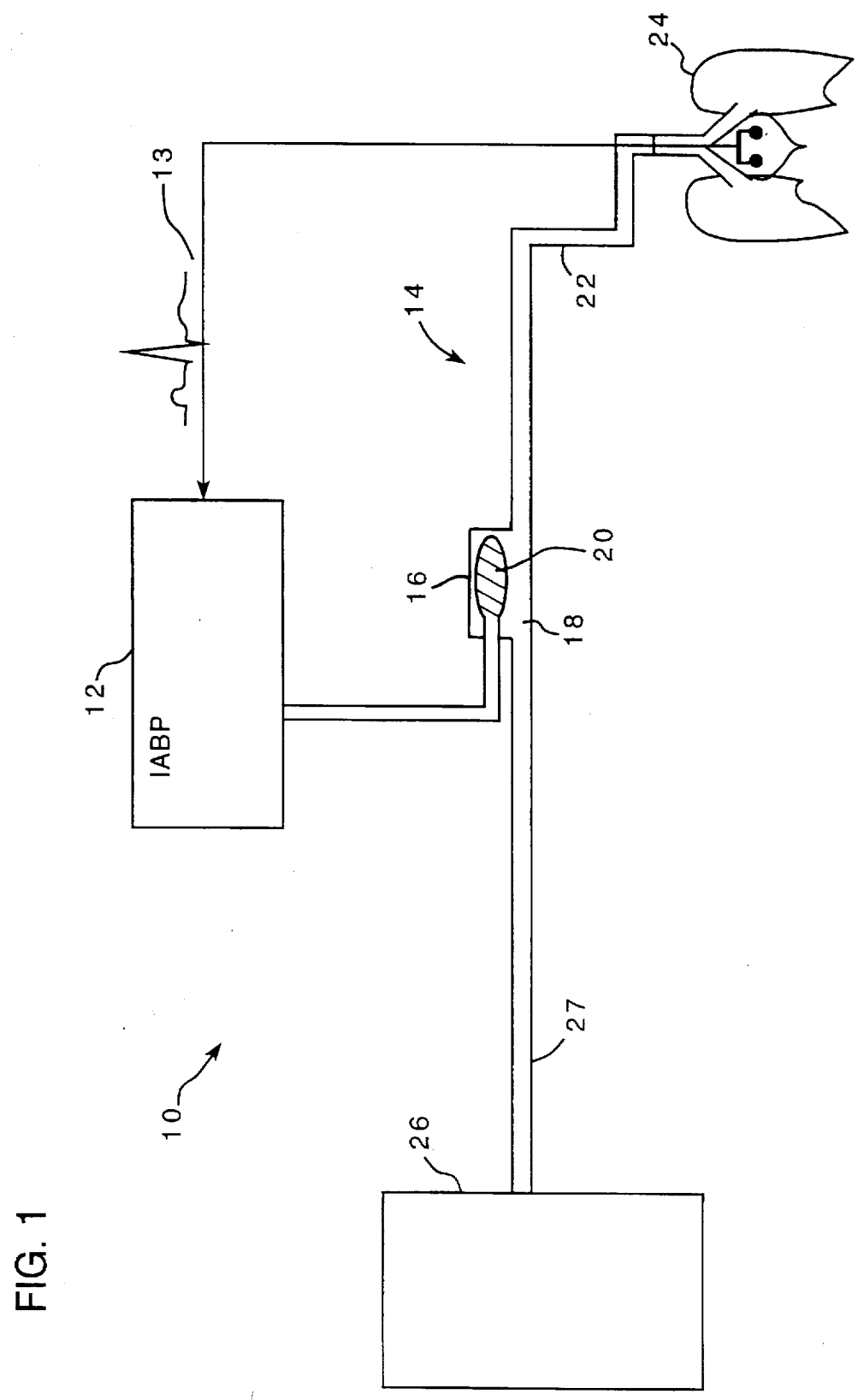
FIG. 1 is a schematic of a cardiac synchronized ventilator.

Referring to FIG. 1, a cardiac synchronized ventilator (CSV) 10, according to the invention, includes a conventional intraaortic balloon pump (IABP) 12 and an output 13 from an EKG (not shown) used to synchronize IABP 12 to the cardiac cycle. A novel, sealed conversion unit 14 enables IABP 12 to function as a cardiac synchronized ventilator. Conversion unit 14 includes a conversion chamber 16 filled with ventilation medium 18, e.g., a gas mixture of air and $O_2$, or a liquid of oxygenated perfluorocarbon. Conversion chamber 16 can be made from, e.g., plexi-glass, and sized to contain, e.g., 1.25 liters of ventilation medium. A balloon 20, such as a standard intraaortic balloon (IAB), is located within chamber 16. Conversion unit 14 further includes a conduction line 22 for transporting ventilation medium 18 from chamber 16 to the lungs 24 of a patient and for transporting ventilation medium from the lungs of the patient. A ventilation medium source 26 supplies ventilation medium 18 to chamber 16 and conduction line 22 via a conduit 27.

CSV 10 delivers breaths on every heartbeat or some fraction thereof, for example, ratios of delivered breath to heartbeat of 1:1, 1:2, and 1:4 (this parameter generally can be selected by a switch on IABP 12), at tidal volumes of about 80 cc for gas and liquid ventilation with a positive pressure swing of about 30 cm $H_2O$ for gas ventilation and 20 cm $H_2O$ for liquid ventilation. Inflation of IAB 20 displaces about 80 cc. To achieve a larger desired tidal volume during gas ventilation, more than one IAB may be utilized in chamber 16 or a balloon capable of displacing a larger volume may replace IAB 20.

Figure 2:
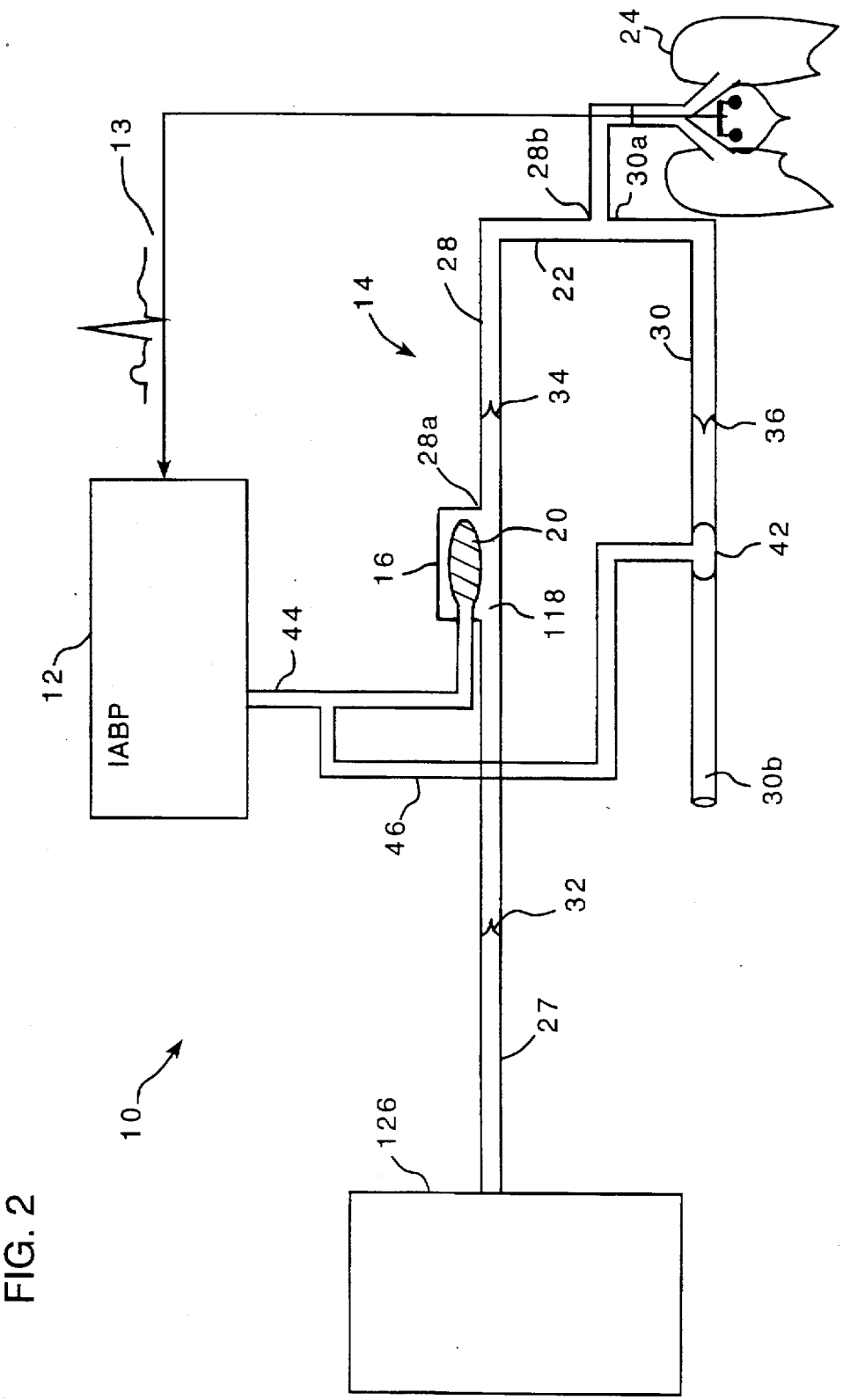
FIG. 2 is a schematic of a cardiac synchronized ventilator for ventilating a patient with a gas.

Referring to FIG. 2, a monophasic gas CSV includes a gas source 126 of a mixture of air and $O_2$ 118. Conduction line 22 includes an inspiratory line 28 having a first end 28a attached to chamber 16 and a second end 28b leading to lungs 24 for conducting gas 118 to lungs 24, and an expiratory line 30 having a first end 30a leading from lungs 24 and a second end 30b open to atmosphere for conducting gas 118 from lungs 24 to atmosphere.

One-way valves 32, 34 and 36, such as are available from Simths Industries, Ft. Myers, Fla., prevent backflow of gas in conduction line 22 and conduit 27 permitting gas flow toward the lungs in conduit 27 and inspiratory line 28 and away from the lungs in expiratory line 30. A valve 42, for example, a balloon valve, closes off expiratory line 30 from the atmosphere to allow pressurization of conduction line 22 when delivering gas to lungs 24. Balloon valve 42 is synchronized to inflate and deflate with IAB 20 by a common connection to a pressure line 44 via a conduit 46.

The lines in which ventilation medium flows to and from the patient's lungs, conduction line 22 and conduit 26, can be constructed, e.g., of clear, flexible PVC tubing having an inner diameter of about ½ inch and an outer diameter of about ¾ inch. The non-fluid moving lines, pressure line 44 and conduit 46, can be constructed, e.g., of clear, flexible tubing having an inner diameter of ¼ inch and an outer diameter of ⅜ inch.

In use, during systole, IABP 12 inflates IAB 20 and balloon valve 42, positively pressurizing conduction line 22, and forcing gas 118 to enter lungs 24. IAB 20 and balloon valve 42 are then deflated allowing spontaneous exhalation. Gas 118 is exhaled through expiratory line 30 to the atmosphere.

Figure 3:
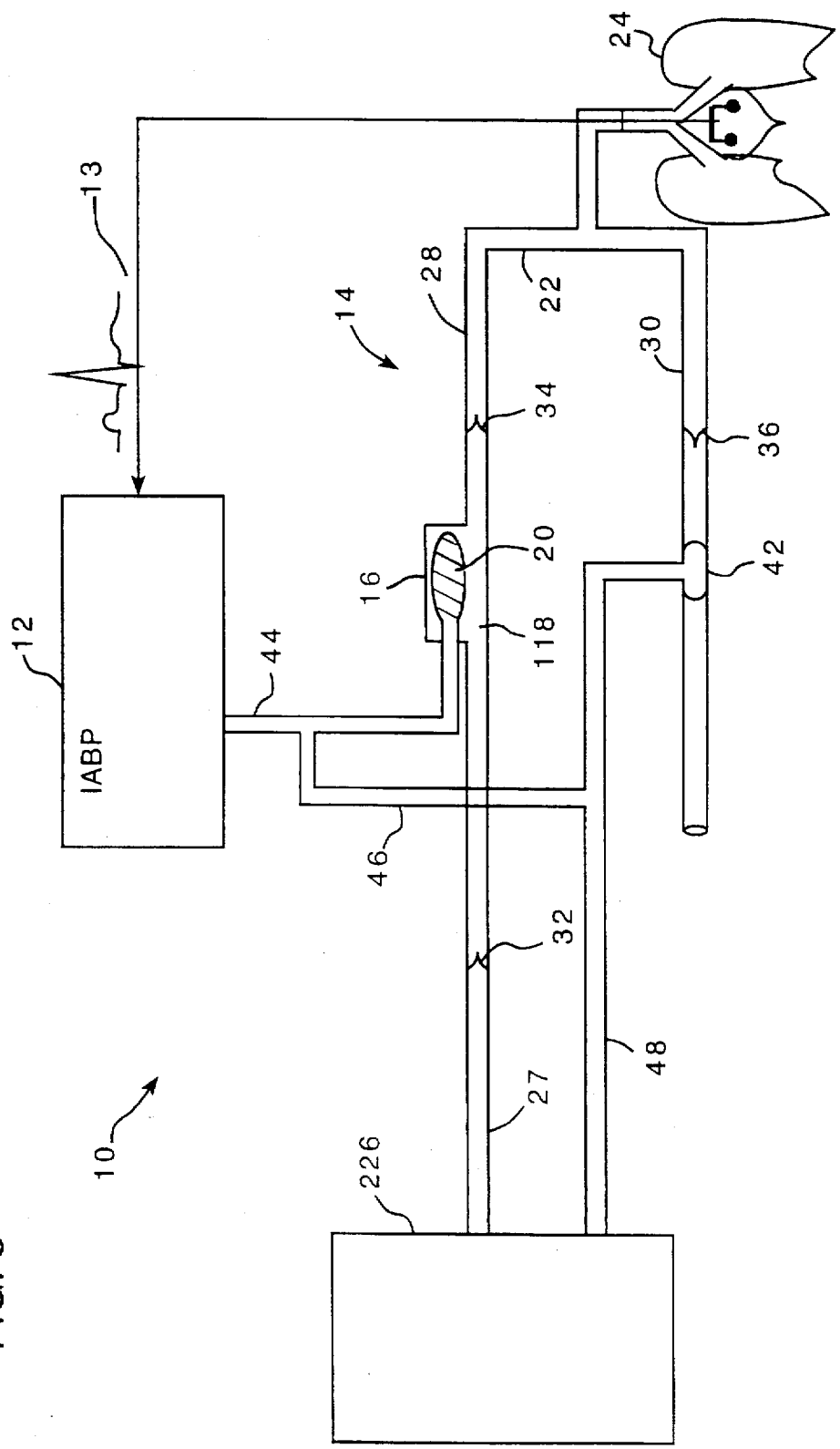
FIG. 3 is a schematic of a cardiac synchronized ventilator for use in conjunction with a standard ventilator.

Referring to FIG. 3, in another embodiment of the invention for use as a monophasic gas CSV, reservoir 126 is replaced with a standard gas ventilator 226, for example, a Puritan Bennett ventilator model number 7200-A. The standard ventilator 226 can be used in conjunction with IABP 12 to deliver a larger volume of gas to lungs 24. Thus, while ventilator 226 is supplying oxygenated gas to lungs 24 at the rate of about 17 breath/minute, the CSV is ventilating the lungs at a rate of about 75 breaths/minute in synchrony with the cardiac cycle to assist cardiac function and at least partly counteract the negative effects of standard ventilation. The CSV delivers gas at tidal volumes of about 80 cc and the standard ventilator 226 is adjusted, either by adjusting its rate or tidal volume, to deliver an additional volume of gas, generally for a total gas volume of about 10 liters/min. The desired gas volume is generally in the range of about 5 to 30 liters/min; below 6.4 liters/min, the CSV alone can deliver the desired gas volume.

To close off expiratory line 30 during positive pressurization of conduction line 22 and conduit 27 by standard ventilator 226, a pressure line 48 runs from standard gas ventilator 226 to balloon valve 42.

Liquid Ventilation

It is known that physiological gas exchange and acid-base status in mature and immature humans and animals can be maintained through liquid breathing techniques ("liquid ventilation"). Oxygenated perfluorocarbon is the liquid ventilation medium of choice. Liquid ventilation is being investigated in the ventilation of diseases which cause high surface tension at the alveoli. The high surface tension causes lung collapse which requires high pressure ventilation when using gas as the ventilation medium. Using liquid eliminates the surface tension thus allowing for ventilation at standard pressure. In addition, the use of a non-compressible liquid as the ventilation medium increases the rigidity of the thorax region improving cardiac output. With liquid ventilation, each tidal volume during inhalation forces about an equal volume of blood to be ejected from the thorax and each exhalation forces about an equal volume of blood to be returned to the thorax.

Figure 4:
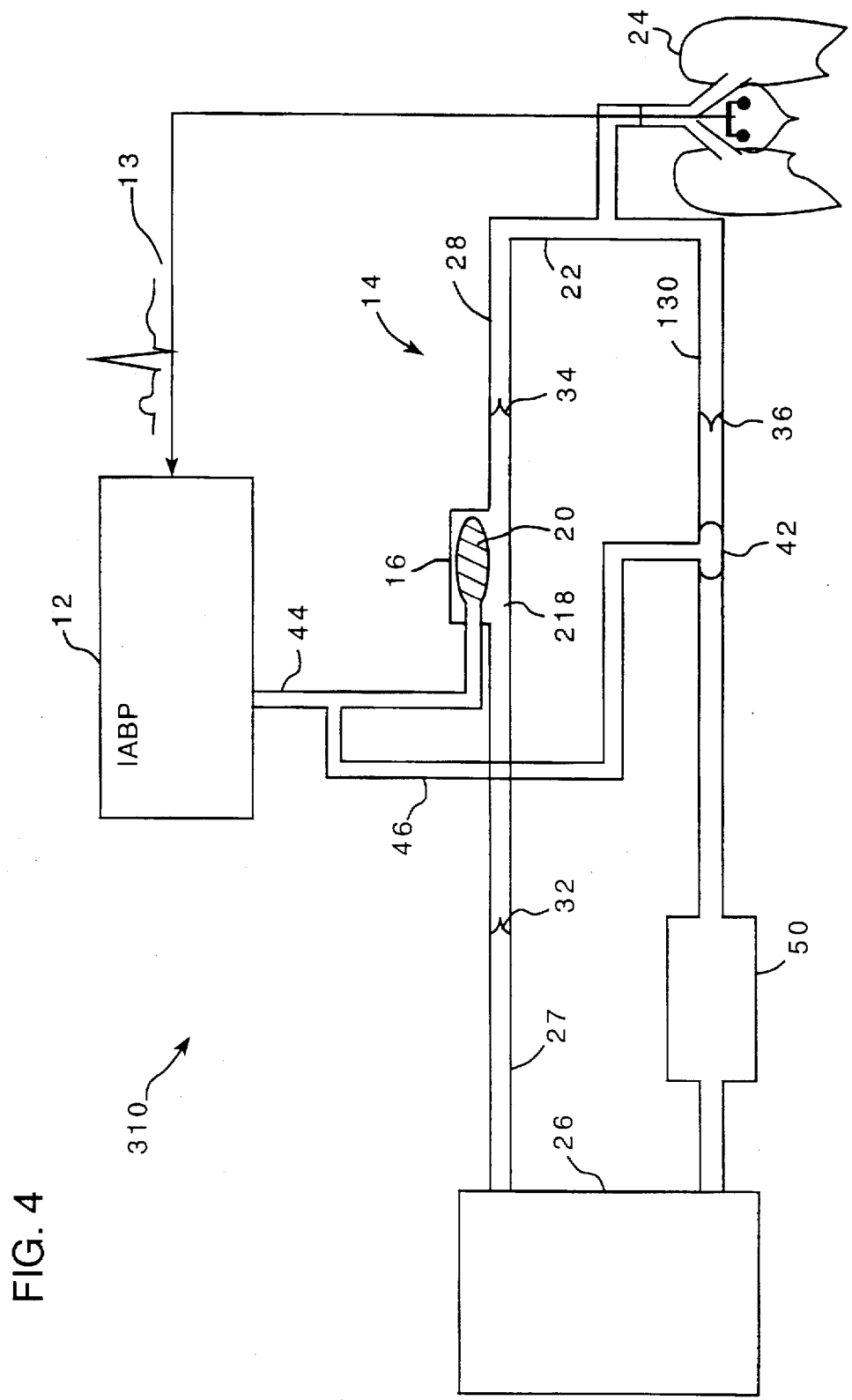
FIG. 4 is a schematic of a cardiac synchronized ventilator for ventilating a patient with a liquid.

Referring to FIG. 4, a monophasic liquid CSV 310 is similar to the monophasic gas CSV of FIG. 2. However, here, expiratory line 130 returns liquid ventilation medium 218 to reservoir 26. A membrane oxygenator 50, made by Avecor, Plymouth, Minn., located in expiratory line 130 reoxygenates the expelled liquid.

During monophasic CSV the normal venous return enhancing negative intrathoracic pressure swing is absent.

The aim of biphasic CSV is to apply a negative pressure pulse to augment cardiac output. The CSV uses small tidal volumes of non-compressible liquid to deliver a period of negative pressure, e.g., about −7 to −8 cm $H_2O$, for such a brief period, e.g., ⅓ of the total cardiac cycle time (peak systole to peak systole), that the small airways which have been seen to collapse in negative pressure ventilation do not collapse.

Figure 5:
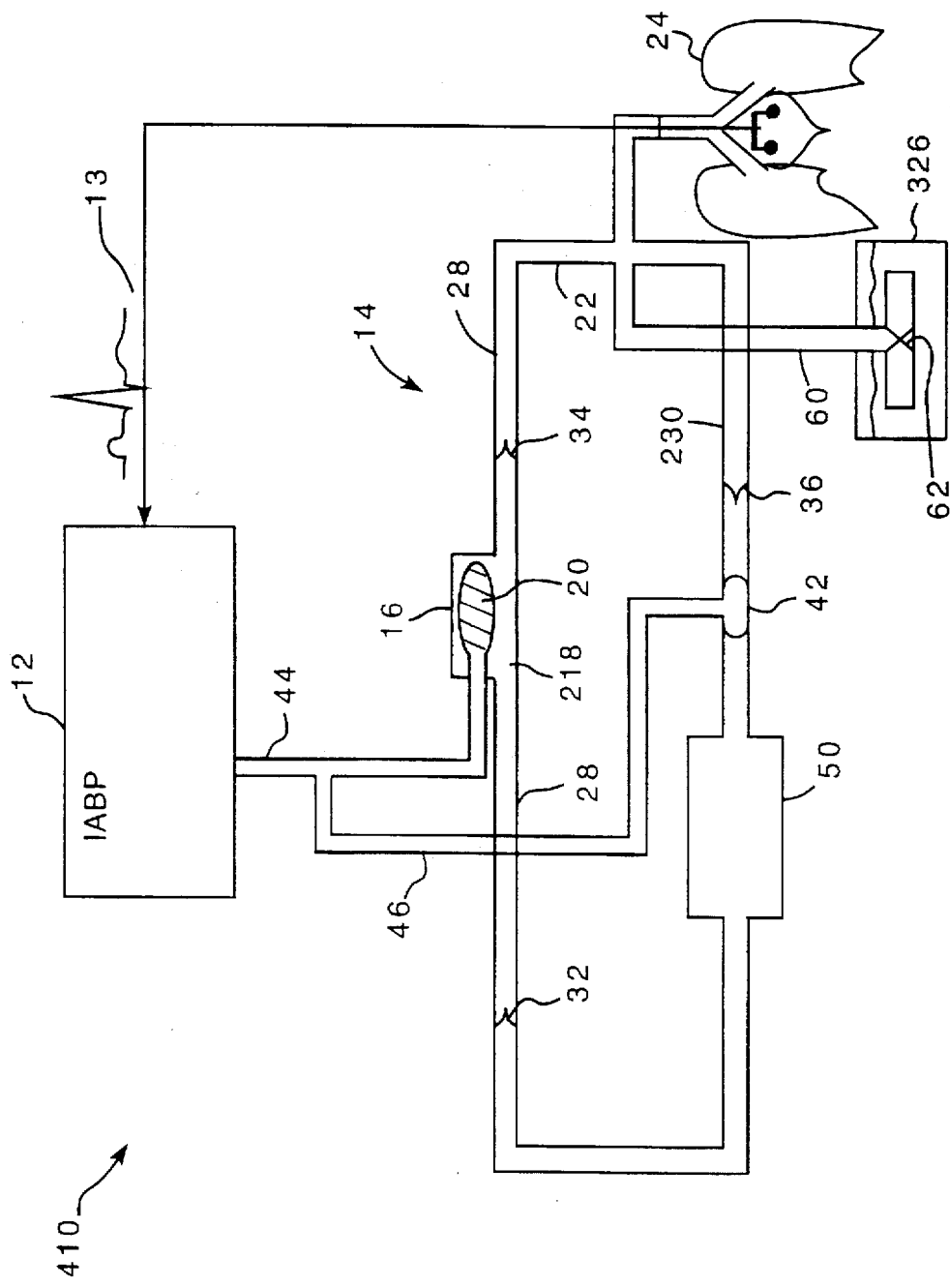
FIG. 5 is a schematic of a cardiac synchronized ventilator for use as a biphasic liquid cardiac synchronized ventilator.

Referring to FIG. 5, a biphasic liquid CSV includes an expiratory line 230 leading back to conversion chamber 16. Deflation of IAB 20 negatively pressurizes conduction line 22 extracting liquid ventilation medium 218 from the patient's lungs 24.

In use, during diastole, IAB 20 is deflated producing a negative pressure in conversion unit 14 forcibly extracting liquid ventilation medium 218 from lungs 24. Deflation of balloon valve 42 allows the liquid ventilation medium to travel down expiratory line 230 and through the membrane oxygenator 50. A conduit 60 runs from conduction line 22 to a reservoir 326. A safety valve 62 opens when the pressure in conduction line 22 falls below a desired value, e.g., −10 cm $H_2O$, allowing additional liquid ventilation medium 218 to enter conduction line 22, and when the pressure in conduction line 22 is above a desired value, e.g., 60 cm $H_2O$, allowing excess ventilation medium to exit conduction line 22.

While the use of liquid ventilation medium is preferable, it is recognized that the embodiment of FIG. 5 could be used for biphasic gas CSV.

Ventilator 10 can be used without synchronization by setting IABP 12 to a desired frequency. A ventilation medium source 26 which includes both gas and liquid sources provides the user with a choice of ventilation medium 18.

Other Embodiments

Other embodiments are within the following claims.

We claim:

1. A cardiac synchronized ventilator for use with a patient, said ventilator comprising:

a balloon;

a balloon pump arranged to inflate and deflate said balloon, said inflation being in synchrony with cardiac function of the patient, and a conversion unit comprising,
      a chamber fillable with a ventilation medium and containing said balloon, and
      one or more conduction lines for containing ventilation medium, said one or more conduction lines being arranged to carry ventilation medium from said chamber to the patient's lungs and arranged to carry ventilation medium from the patient's lungs;

whereby, said balloon is inflated during systole of the patient's heart, and said inflation pressurizes said conduction line to deliver ventilation medium to the patient's lungs.

2. A cardiac synchronized ventilator of claim 1, wherein said pump is an intraaortic balloon pump.

3. A cardiac synchronized ventilator of claim 1, wherein said conduction line comprises an inspiratory line connecting said chamber to the patient's lungs for conducting oxygenated ventilation medium to the patient's lungs, and an expiratory line for conducting deoxygenated ventilation medium from the patient's lungs.

4. A cardiac synchronized ventilator of claim 3, further comprising a conduit connected to a source of ventilation medium, said conduit being in fluid communication with said conduction line.

5. A cardiac synchronized ventilator of claim 4, wherein said inspiratory line, said expiratory line, and said conduit include valves preventing backflow of said ventilation medium.

6. A cardiac synchronized ventilator of claim 5, further including a valve synchronized to inflation of said balloon to close said expiratory line when said balloon is inflated.

7. A cardiac synchronized ventilator of claim 6, wherein said synchronized valve is a balloon valve.

8. A cardiac synchronized ventilator of claim 6, wherein the ventilation medium is a gas and said expiratory line conducts the gas from the patient's lungs to atmosphere upon deflation of said balloon.

9. A cardiac synchronized ventilator of claim 8, wherein said source is a ventilator.

10. A cardiac synchronized ventilator of claim 9, wherein said ventilator controls said synchronized valve to close said expiratory line when conducting oxygenated ventilation medium to the patient's lungs, said ventilator and said cardiac synchronized ventilator are constructed and arranged to ventilate the patient concurrently.

11. A cardiac synchronized ventilator of claim 6, wherein said ventilation medium is a liquid and said source is a reservoir of the liquid.

12. A cardiac synchronized ventilator of claim 11, wherein said expiratory line conducts the liquid from the patient's lungs to the reservoir upon deflation of said balloon.

13. A cardiac synchronized ventilator of claim 11, wherein said expiratory line conducts the liquid from the patient's lungs to said chamber.

14. A cardiac synchronized ventilator of claim 13, wherein the deflation of said balloon is synchronized to occur during diastole.

15. A cardiac synchronized ventilator of claim 14, wherein said conduction line is a closed system such that deflation of said balloon during diastole negatively pressurizes said conduction line to remove ventilation medium from the patient's lungs.

16. A cardiac synchronized ventilator of claim 13, wherein said conduit includes a valve allowing uptake of liquid from said reservoir to said conduction line at a first conduction line pressure, and delivery of liquid from said conduction line to said reservoir at a second conduction line pressure greater than the first conduction line pressure.

17. A cardiac synchronized ventilator of claim 11, further including a membrane oxygenator for oxygenating the liquid.

18. A balloon pump converter for converting an intraaortic balloon pump into a cardiac synchronized ventilator, comprising:
- a conversion chamber for interfacing with the intraaortic balloon pump and for containing a balloon associated with the intraaortic balloon pump, said conversion chamber being fillable with ventilation medium, and
- a conduction line connected to said chamber for conducting ventilation medium to and from a patient's lungs.

19. A balloon pump converter of claim 18, wherein said ventilation medium is a liquid or gas.

20. A ventilator capable of delivering liquid or gas to the pulmonary system of a patient, comprising:
- a balloon;
- a balloon pump for inflating and deflating said balloon; and
- a conversion unit comprising,
    - a chamber fillable with the gas or liquid and containing said balloon, and
    - a conduction line for containing the gas or liquid and arranged to carry the gas or liquid from said chamber to and from a patient's lungs;

whereby, inflation of said balloon pressurizes said conduction line to deliver the gas or liquid to the patient's lungs.

21. A ventilator of claim 20, wherein said balloon is an intraaortic balloon.

* * * * *